(12) United States Patent
Takahashi et al.

(10) Patent No.: US 11,646,454 B2
(45) Date of Patent: May 9, 2023

(54) LIQUID DETECTION SENSOR

(71) Applicant: FUJIKURA COMPOSITES Inc., Tokyo (JP)

(72) Inventors: Masaki Takahashi, Saitama (JP); Masahiro Seshimo, Saitama (JP)

(73) Assignee: FUJIKURA COMPOSITES INC., Tokyo (JP)

( * ) Notice: Subject to any disclaimer, the term of this patent is extended or adjusted under 35 U.S.C. 154(b) by 0 days.

(21) Appl. No.: 17/625,185

(22) PCT Filed: May 27, 2020

(86) PCT No.: PCT/JP2020/020954
§ 371 (c)(1),
(2) Date: Jan. 6, 2022

(87) PCT Pub. No.: WO2021/005906
PCT Pub. Date: Jan. 14, 2021

(65) Prior Publication Data
US 2022/0278380 A1 Sep. 1, 2022

(30) Foreign Application Priority Data

Jul. 10, 2019 (JP) .............................. JP2019-128089
Sep. 10, 2019 (JP) .............................. JP2019-164902

(51) Int. Cl.
*H01M 10/42* (2006.01)
*H01M 4/46* (2006.01)
(Continued)

(52) U.S. Cl.
CPC ......... *H01M 10/4228* (2013.01); *G01M 3/16* (2013.01); *H01M 4/46* (2013.01); *H01M 12/06* (2013.01)

(58) Field of Classification Search
None
See application file for complete search history.

(56) References Cited

U.S. PATENT DOCUMENTS 4,855,706 A 8/1989 Hauptly
6,127,061 A * 10/2000 Shun .................... H01M 12/06
429/165
(Continued)

FOREIGN PATENT DOCUMENTS

CN 102308414 A 1/2012
CN 104977319 A 10/2015
(Continued)

OTHER PUBLICATIONS https://www.flyingmag.com/everything-you-need-to-know-about-emergency-locator-transmitters/ (Year: 2018).*
(Continued)

*Primary Examiner* — Lisa S Park
(74) *Attorney, Agent, or Firm* — McCormick, Paulding & Huber PLLC

(57) ABSTRACT

Particularly, there is provided a liquid detection sensor in which a liquid contact area is formed integrally with a separator, and that improves detection accuracy with a small number of parts. A liquid detection sensor (1) according to the present invention includes a metal-air battery (2) formed by laminating a negative electrode sheet (3), a positive electrode sheet (5) and a separator (4) interposed between the negative electrode sheet (3) and the positive electrode sheet (5), and the separator (4) is formed wider than an area in which the positive electrode sheet (5) and the negative electrode sheet (3) overlap with the separator (4) interposed therebetween, and includes a liquid contact area (4') exposed from at least one of the positive electrode sheet and the negative electrode sheet.

9 Claims, 9 Drawing Sheets

(51) Int. Cl.
    *H01M 12/06*    (2006.01)
    *G01M 3/16*     (2006.01)

(56) References Cited

U.S. PATENT DOCUMENTS

| | | | |
|---|---|---|---|
| 2010/0203394 A1* | 8/2010 | Bae | H01M 50/489 |
| | | | 429/246 |
| 2011/0059364 A1* | 3/2011 | Zhang | H01M 4/133 |
| | | | 156/285 |
| 2014/0205909 A1* | 7/2014 | Yonehara | H01M 10/4235 |
| | | | 429/300 |
| 2015/0283281 A1* | 10/2015 | Iwaki | G01F 23/00 |
| | | | 422/119 |
| 2016/0166757 A1 | 6/2016 | Koyama et al. | |
| 2016/0204437 A1 | 7/2016 | Tajima et al. | |
| 2018/0058975 A1 | 3/2018 | Li et al. | |

FOREIGN PATENT DOCUMENTS

| | | |
|---|---|---|
| CN | 105263395 A | 1/2016 |
| JP | 2006-53057 A | 2/2007 |
| JP | 2012-517075 A | 7/2012 |
| JP | 2015-197392 A | 11/2015 |
| JP | 2016-102771 A | 6/2016 |
| JP | 2016-136516 A | 7/2016 |
| JP | 2017-148332 A | 8/2017 |
| WO | 2012020507 A1 | 10/2013 |

OTHER PUBLICATIONS

Office Action issued for Chinese Patent Application No. 202080047515.0 dated Jul. 15, 2022.

\* cited by examiner

LIQUID DETECTION SENSOR

CROSS-REFERENCE TO RELATED APPLICATION

This application is a National Stage application of International Patent Application No. PCT/JP2020/020954 filed on May 27, 2020, and claims priority to Japanese Patent Application No. 2019-128089 filed on Jul. 10, 2019, and Japanese Patent Application No. 2019-164902 filed on Sep. 10, 2019 the entire contents of which are incorporated by reference herein.

TECHNICAL FIELD

The present invention relates to a liquid detection sensor that includes a metal-air battery.

BACKGROUND

A liquid leakage detection system is used at medical settings or indoor workplaces. According to the liquid leakage detection system, a liquid detection sensor is disposed at a liquid leakage portion. The liquid detection sensor captures an electrical change caused upon contact of a liquid from an outside, and detects liquid leakage.

For example, WO Patent No. 2012/020507 and Japanese Patent No. 2017-148332 disclose inventions that relate to liquid leakage detection systems for blood leakage detection. The invention described in WO Patent No. 2012/020507 discloses a sensor that uses a water battery that generates electric power by using a leaking liquid. The invention described in Japanese Patent No. 2017-148332 discloses a sensor that uses a magnesium battery that includes a positive electrode sheet, a separator and a negative electrode sheet.

SUMMARY

According to the invention that is described in WO Patent No. 2012/020507 and uses the water battery, the water battery is disposed on an upper side of or inside an absorbable member, and a liquid such as blood widely permeates to the absorbable member, causes an electrochemical reaction inside the water battery, and thereby causes the water battery to generate electric power.

Thus, WO Patent No. 2012/020507 requires the absorbable member in addition to the water battery, and, if a liquid of a substantial amount does not permeate to the absorbable member, it is not possible to appropriately detect liquid leakage.

According to the invention that is described in Japanese Patent No. 2017-148332 and uses the magnesium battery, a liquid leakage sensor section is housed between a back adhesive bandage and a top adhesive bandage, and a leaking liquid permeates from the back adhesive bandage to an interior of the liquid leakage sensor section, causes an electrochemical reaction, and causes the magnesium battery to generate electric power.

Thus, according to Japanese Patent No. 2017-148332, it is necessary to make the liquid permeate from the back adhesive bandage to a separator of the liquid leakage sensor section, and therefore it is not possible to make the liquid appropriately permeate to the separator depending on a liquid leakage amount, and detection accuracy is likely to lower.

The present invention has been made in light of the above point, and, more particularly, an object of the present invention is to provide a liquid detection sensor in which a liquid contact area is integrally formed with a separator and that improves detection accuracy without increasing the number of parts.

According to a liquid detection sensor according to the present invention, a positive electrode sheet, a negative electrode sheet and a separator interposed between the positive electrode sheet and the negative electrode sheet are laminated to form a metal-air battery, and the separator is formed wider than an area in which the positive electrode sheet and the negative electrode sheet overlap with the separator interposed therebetween, and includes a liquid contact area exposed from at least one of the positive electrode sheet and the negative electrode sheet.

The present invention can adopt a structure that the liquid contact area is formed on an outer side of an outer circumference end part of one or both of the positive electrode sheet and the negative electrode sheet.

The present invention can adopt a structure that the liquid contact area is formed extending from outer circumference end parts of both of the positive electrode sheet and the negative electrode sheet.

The present invention can adopt a structure that the liquid contact area is bent toward an outer face side of at least one of the positive electrode sheet and the negative electrode sheet.

The present invention can adopt a structure that the liquid contact area is formed on an inner side of an outer circumference end part of one or both of the positive electrode sheet and the negative electrode sheet.

The present invention can adopt a structure that one or a plurality of holes that penetrate to the separator are formed in one or both of the positive electrode sheet and the negative electrode sheet, and parts of the separator that are exposed through the holes are the liquid contact areas.

The present invention can adopt a structure that the separator is separated into a plurality of separators, and the liquid contact area is formed with each separator.

According to the present invention, the negative electrode sheet is preferably a magnesium sheet or a magnesium alloy sheet.

The present invention preferably includes a transmission section that can communicate a detection signal of the metal-air battery by radio to a reception section.

According to the present invention, the liquid detection sensor is, for example, a blood leakage detection sensor or a water leakage detection sensor.

According to the liquid detection sensor according to the present invention, the separator that makes up the metal-air battery is formed larger than the overlapping area of the positive electrode sheet and the negative electrode sheet, and the part exposed from the positive electrode sheet or the negative electrode sheet is the liquid contact area. Consequently, it is easy to make the liquid that has contacted the liquid contact area smoothly permeate to the separator between the positive electrode sheet and the negative electrode sheet, and it is possible to improve detection accuracy without increasing the number of parts.

DETAILED DESCRIPTION

One embodiment (abbreviated as an "embodiment" below) according to the present invention will be described in detail below. In this regard, the present invention is not limited to following embodiments, and can be variously modified within a range of a gist of the present invention and carried out.

Figure 1A:
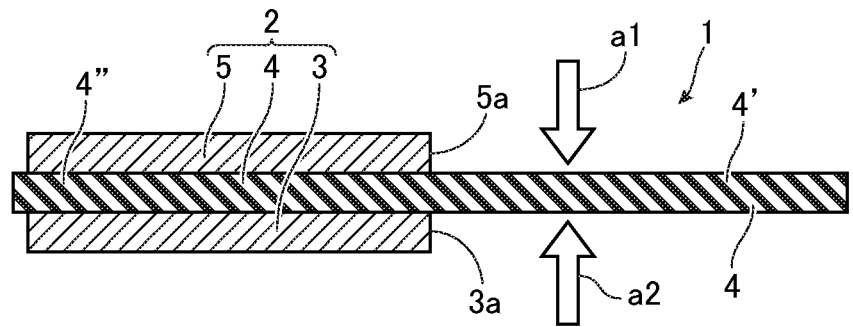
FIG. 1A is a longitudinal cross-sectional view of a liquid detection sensor according to a first embodiment.
Figure 1B:
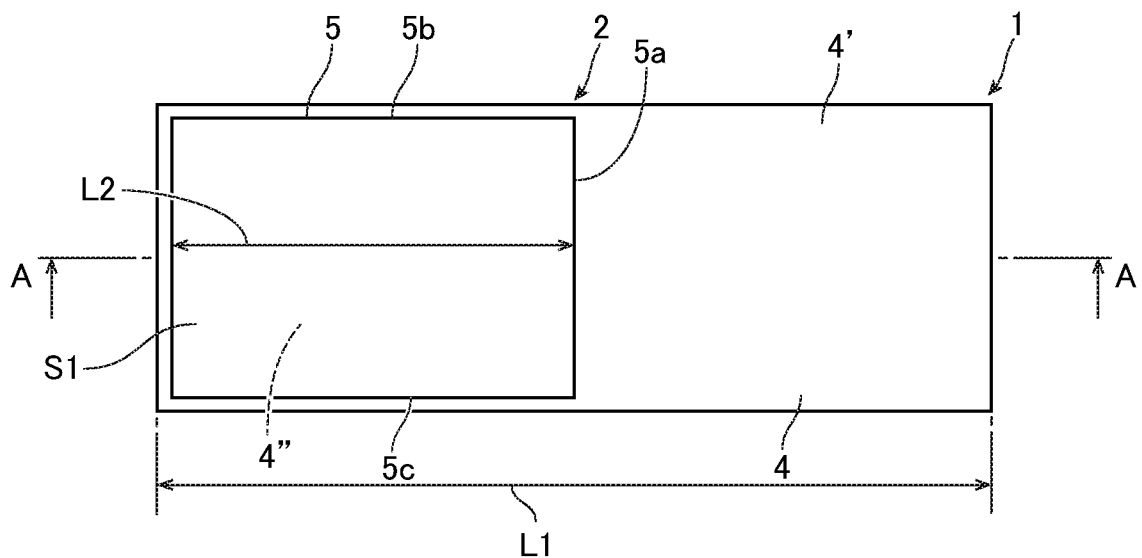
FIG. 1B is a plan view of the liquid detection sensor according to the first embodiment.
Figure 10:
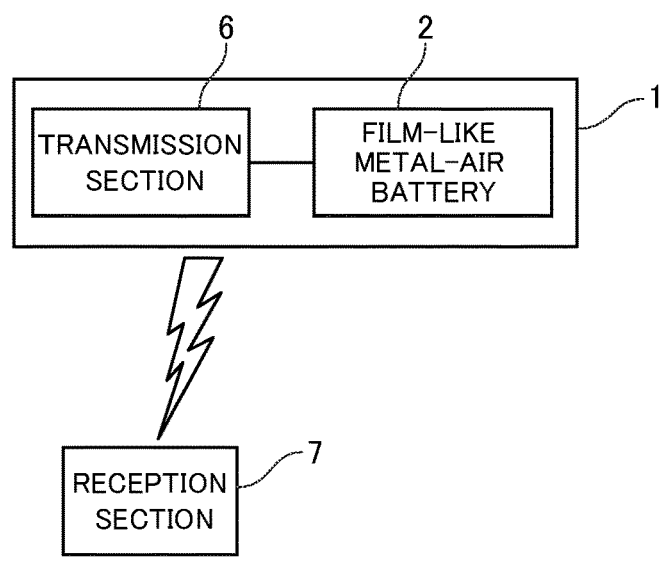
FIG. 10 is a block diagram of a liquid detection sensor according to the present embodiment.

A liquid detection sensor (liquid leakage detection sensor) 1 illustrated in FIGS. 1A and 1B includes a metal-air battery 2. As illustrated in FIG. 10, the liquid detection sensor 1 further includes a transmission section 6. In addition, FIG. 1A is a cross-sectional view cut along a line A-A illustrated in FIG. 1B and seen from an arrow direction.

As illustrated in FIG. 1A, the metal-air battery 2 adopts a laminated structure formed by laminating a negative electrode sheet (metal electrode sheet) 3, a separator 4 and a positive electrode sheet (air electrode sheet) 5. As illustrated in FIG. 1A, the separator 4 is interposed between the negative electrode sheet 3 and the positive electrode sheet 5.

Although a fixing method is not limited, the respective sheets are fixed with an adhesive layer interposed therebetween, fixed by using an outer sheet described later or fixed by a housing such as a plastic housing. Preferably, the adhesive layer is partially provided at rim parts of the negative electrode sheet 3 and the positive electrode sheet 5, and is not provided in a detection area 4" of the separator 4. In this regard, the detection area 4" refers to an area corresponding to a part at which the negative electrode sheet 3 and the positive electrode sheet 5 overlap with the separator 4 interposed therebetween.

Metal that is a constituent of the negative electrode sheet 3 is preferably one of magnesium (Mg), a Mg alloy, zinc (Zn), a Zn alloy, aluminum (Al) and an Al alloy. Metal of these metals that are constituents of the negative electrode sheet 3 is more preferably Mg or the Mg alloy.

The separator 4 is formed by a material having an electrical insulation property, ionic permeability and liquid permeability. The material is, for example, a non-woven fabric, a woven fabric or a porous thin film.

The positive electrode sheet 5 is formed to include a current collector and a catalyst layer (reaction site). Characteristics demanded for the current collector are conductivity that conducts electrons emitted from the negative electrode sheet 3 to the catalyst layer, and breathability that allows oxygen to permeate. Although the structure of the current collector is not limited, for example, existing components such as a wire mesh or foamed metal can be used. Furthermore, characteristics demanded for the catalyst layer are hydrophobicity that does not discharge a liquid outside, and breathability that allows oxygen to permeate. Existing materials can be used for the catalyst layer. The catalyst layer is formed on at least one face of the current collector, and the catalyst layer is in close contact with the separator 4.

As illustrated in FIGS. 1A and 1B, the separator 4 is formed larger than the negative electrode sheet 3 and the positive electrode sheet 5. According to the structure illustrated in FIGS. 1A and 1B, the positive electrode sheet 5 and the negative electrode sheet 3 have the same size.

As illustrated in FIGS. 1A and 1B, the separator 4 extends long toward an illustrated right direction from outer circumference end parts 3a and 5a on an illustrated right side of the negative electrode sheet 3 and the positive electrode sheet 5. In this embodiment, the separator 4 protrudes more or less from an outer circumference end part 5b (an outer circumference end part of the negative electrode sheet 3 is not shown) on an illustrated upper side and an outer circumference end part 5c (an outer circumference end part of the negative electrode sheet 3 is not shown) on an illustrated lower side of the negative electrode sheet 3 and the positive electrode sheet 5. Thus, by forming width dimensions in an illustrated upper-lower direction of the separator 4 larger than those of the positive electrode sheet 5 and the negative electrode sheet 3, too, it is possible to appropriately adjust positions of the positive electrode sheet 5 and the negative electrode sheet 3 in the illustrated upper-lower direction on the separator 4. Consequently, it is possible to appropriately interpose the separator 4 in an entire area between the positive electrode sheet 5 and the negative electrode sheet 3.

The separator 4 includes a liquid contact area 4' that extends from the outer circumference end parts 3a and 5a of the negative electrode sheet 3 and the positive electrode sheet 5, and the detection area 4" that is interposed between the negative electrode sheet 3 and the positive electrode sheet 5. The liquid contact area 4' and the detection area 4" are integrally formed.

In addition, as illustrated in FIG. 1B, the separator 4 is formed to have a length L1 in an illustrated left-right direction. Furthermore, the negative electrode sheet 3 and the positive electrode sheet 5 (only the positive electrode sheet 5 is illustrated in FIG. 1B) is formed to have lengths L2 in the illustrated left-right direction. A length ratio (L1/L2) is, but not limited to, 1.1 to 4.0. As illustrated in FIG. 1B, the negative electrode sheet 3 and the positive electrode sheet 5 are disposed closer to an illustrated left side of a center of the left-right direction of the separator 4. In this way, the liquid contact area 4' is formed on the illustrated right side of the outer circumference end parts 3a and 5a of the negative electrode sheet 3 and the positive electrode sheet 5. Furthermore, it is preferable to dispose the negative electrode sheet 3 and the positive electrode sheet 5 on an inner side more or less from the illustrated left end of the separator 4 instead of aligning the illustrated left end of the separator 4 and the left ends of the negative electrode sheet 3 and the positive electrode sheet 5.

The thickness of the positive electrode sheet 5 (including the current collector) is, but not limited to, approximately 0.4 mm to 2.0 mm. Furthermore, the thickness of the negative electrode sheet 3 is, but not limited to, approximately 0.05 mm to 2.0 mm.

As illustrated in FIG. 1A, a liquid contacts the liquid contact area 4' of the separator 4 from at least one direction of arrows a1 and a2. Furthermore, the liquid permeates from the liquid contact area 4' to the detection area 4". When the liquid reaches the detection area 4", and in a case where, for example, the metal that is a constituent of the negative electrode sheet 3 is, for example, Mg, the negative electrode sheet 3 side causes an oxidation reaction indicated by following (1). Furthermore, the positive electrode sheet 5 causes a reduction reaction indicated by following (2). Accordingly, the entire metal-air battery 2 causes a reaction indicated by following (3), and discharges electric power.

$$2Mg \rightarrow 2Mg^{2+} + 4e^- \quad (1)$$

$$O_2 + 2H_2O + 4e^- \rightarrow 4OH^- \quad (2)$$

$$2Mg + O_2 + 2H_2O \rightarrow 2Mg(OH)_2 \quad (3)$$

According to the embodiment illustrated in FIGS. 1A and 1B, the liquid contact area 4' is formed only in the illustrated right direction seen from the negative electrode sheet 3 and the positive electrode sheet 5, yet may be further formed in an illustrated upper direction, an illustrated lower direction or an illustrated left direction. Thus, the liquid contact areas 4' can be provided in two or more directions. It is possible to widen a liquid leakage detection range by providing the liquid contact areas 4' in the two or more directions.

In FIGS. 1A and 1B, the liquid contact area 4' is extended long outward from the outer circumference end parts 3a and 5a of the negative electrode sheet 3 and the positive electrode sheet 5, so that it is possible to appropriately detect liquid leakage at portions distant from the negative electrode sheet 3 and the positive electrode sheet 5, too.

Figure 2:
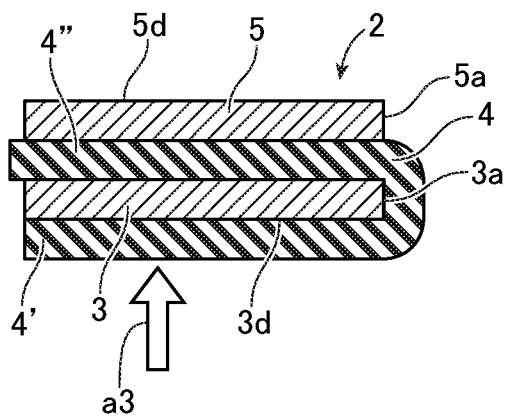
FIG. 2 is a longitudinal cross-sectional view of a liquid detection sensor according to a second embodiment.

On the other hand, according to the second embodiment illustrated in FIG. 2, a separator 4 extending from outer circumference end parts 3a and 5a of a negative electrode sheet 3 and a positive electrode sheet 5 is bent so as to overlap an outer face 3d (a lower face of the negative electrode sheet 3 illustrated in FIG. 2) of the negative electrode sheet 3. Consequently, it is possible to dispose a liquid contact area 4' so as to overlap the negative electrode sheet 3 and the positive electrode sheet 5.

According to the embodiment illustrated in FIG. 2, due to liquid leakage from a direction of an arrow a3 and surroundings of a metal-air battery 2, the liquid contacts the liquid contact area 4'. Then, the liquid quickly permeates from the liquid contact area 4' to a detection area 4" sandwiched between the negative electrode sheet 3 and the positive electrode sheet 5, so that it is possible to accurately detect liquid leakage.

The metal-air battery 2 according to the embodiment illustrated in FIG. 2 can realize miniaturization compared to the metal-air battery 2 illustrated in FIG. 1A, and is particularly superior for use in intensively detecting liquid leakage at predetermined portions. When, for example, the metal-air battery 2 is used for detection of bleeding, it is possible to intensively detect bleeding at a predetermined portion of a human body by applying the metal-air battery 2 illustrated in FIG. 2 to a part of the human body that needs to be detected. Furthermore, by forming multiple micropores in the negative electrode sheet 3 illustrated in FIG. 2, the liquid that has contacted the liquid contact area 4' can pass through the micropores and reach the detection area 4", so that it is possible to more quickly detect liquid leakage.

In addition, although the direction in which the separator 4 extending from the outer circumference end parts 3a and 5a of the negative electrode sheet 3 and the positive electrode sheet 5 is bent may be either one of the outer face 3d side of the negative electrode sheet 3 or an outer face 5d side of the positive electrode sheet 5, when the separator 4 is bent toward the positive electrode sheet 5 side, the positive electrode sheet 5 needs to contact air, and therefore needs to adopt a structure that allows contact with air. Hence, bending the separator 4 so as to overlap the outer face 3d of the negative electrode sheet 3 is preferable since it is possible to simplify the structure without blocking contact of the positive electrode sheet 5 side with air. In this regard, although not illustrated in FIGS. 1A and 1B, for example, an outer sheet that protects the metal-air battery 2 is preferably provided so as to cover a surface of a laminated part of the metal-air battery 2 in particular at which the negative electrode sheet 3, the separator 4 and the positive electrode sheet 5 are laminated. In this case, the outer sheet is disposed such that air can contact the positive electrode sheet 5. For example, one or a plurality of holes are formed in the outer sheet, and the holes continue to the positive electrode sheet 5. Furthermore, multiple micropores are formed at parts of the outer sheet that cover the liquid contact area 4', or the outer sheet is formed by using a material that allows a liquid to permeate such that the liquid contacts the liquid contact area 4' through the outer sheet at portions at which the outer sheet covers the liquid contact area 4'.

Furthermore, the liquid contact area 4' is provided on a lower side of the metal-air battery 2 according to the embodiment illustrated in FIG. 2. However, the metal-air battery 2 illustrated in FIG. 2 may be turned upside down such that the liquid contact area 4' is disposed on an upper side thereof.

Furthermore, each embodiment illustrated in FIGS. 1A and 2 may be combined to adopt a structure that the separator 4 is formed as a plurality of layers of separators, the one separator 4 is extended long outward from the outer circumference end parts 3a and 5a of the negative electrode sheet 3 and the positive electrode sheet 5 as illustrated in FIG. 1A, and the other separator 4 is bent as illustrated in FIG. 2.

In addition, a planar shape of the separator 4 is not limited to the shape in FIG. 1B, and the detection area 4" may adopt, for example, a structure that the liquid contact area 4' is not separated yet a cut is formed in part or entirety of the liquid contact area 4'.

Figure 3A:
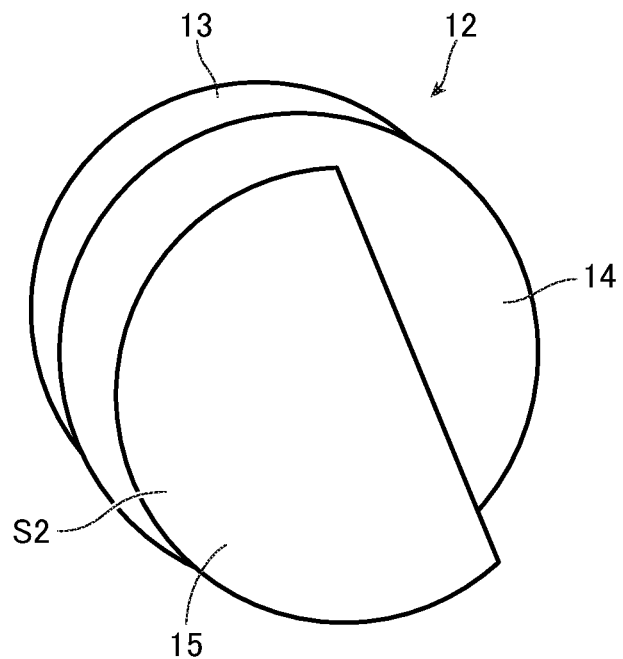
FIG. 3A is an exploded plan view of a liquid detection sensor according to a third embodiment.
Figure 3B:
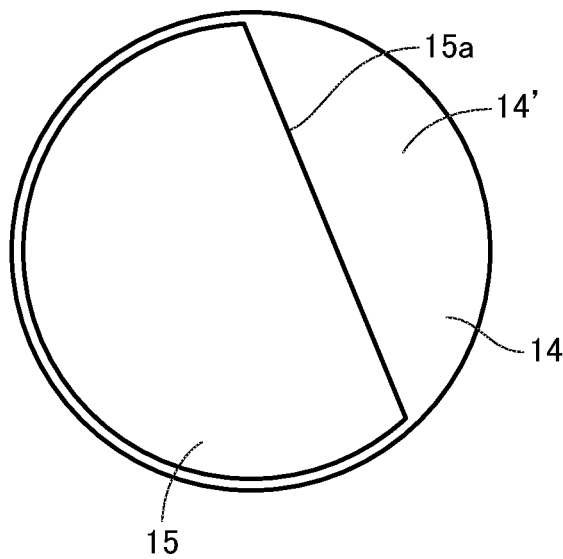
FIG. 3B is a plan view of the liquid detection sensor according to the third embodiment.
Figure 3C:
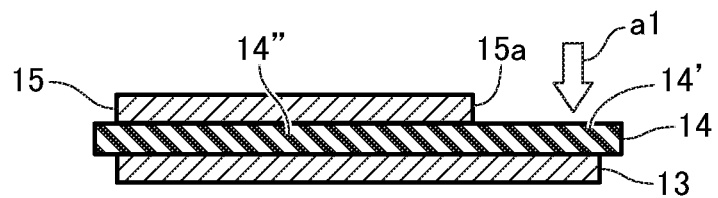
FIG. 3C is a longitudinal cross-sectional view of the liquid detection sensor according to the third embodiment.

FIG. 3A is an exploded plan view of a liquid detection sensor according to the third embodiment, FIG. 3B is a plan view, and FIG. 3C is a longitudinal cross-sectional view. The "exploded plan view" shifts and illustrates each of a negative electrode sheet 13, a separator 14 and a positive electrode sheet 15. The same applies to FIG. 4 and subsequent drawings, too.

A metal-air battery 12 illustrated in FIGS. 3A to 3C adopts, for example, a laminated structure formed by laminating the negative electrode sheet 13 of a circular shape, the separator 14 of a circular shape and the positive electrode sheet 15 of a shape formed by cutting part of a circular shape. Therefore, the positive electrode sheet 15 is formed to have a smaller area than those of the negative electrode sheet 13 and the separator 14. In addition, the separator 14 is formed more or less larger than the negative electrode sheet 13 (see FIG. 3C). According to the present embodiment, as illustrated in FIGS. 3B and 3C, a liquid contact area 14' that is exposed toward an outer side compared to an outer circumference end part 15a on a cutout side of the positive electrode sheet 15 is formed with the separator 14. Furthermore, the separator 14 is provided with a detection area 14" as a part at which the negative electrode sheet 13 and the positive electrode sheet 15 overlap with the separator 14 interposed therebetween.

As illustrated in FIG. 3C, a liquid contacts the liquid contact area 14' of the separator 14 from a direction of an arrow a1. Then, the liquid permeates from the liquid contact area 14' to the detection area 14", so that reactions indicated by above (1) to (3) occur, and electric power is discharged.

In addition, the positive electrode sheet 15 may be formed in, for example, a circular shape similar to that of the separator 14, and the negative electrode sheet 13 may be formed in a shape having a smaller area than that of the circular shape of the positive electrode sheet 15. In this case, the liquid contact area 14" of the separator 14 is provided on an outer side of the outer circumference end part of the negative electrode sheet 13. According to this structure, for example, the negative electrode sheet 13 is disposed facing a side that contacts the liquid. In this case, even when the amount of the liquid is large and the negative electrode sheet 13 side is blocked from contacting air, as long as the positive electrode sheet 15 side can keep contact with the air, it is possible to cause the metal-air battery 12 to appropriately operate. Therefore, in a case where the amount of a liquid that contacts the metal-air battery 12 is large, it is preferable to form the negative electrode sheet 13 side of a small area, and provide the liquid contact area 14' on the outer circumference end part side of the negative electrode sheet 13. In addition, it is also possible to make a structure that both of the negative electrode sheet 13 and the positive electrode sheet 15 are formed to have smaller areas than that of the separator 14, and the liquid contact area 14" is exposed from the respective outer circumference end parts of the negative electrode sheet 13 and the positive electrode sheet 15. In this regard, the structure that the liquid contact area 14' is exposed from the outer circumference end parts on the same side of the negative electrode sheet 13 and the positive electrode sheet 15 is similar to the structure in FIG. 1A. Furthermore, it is also possible to expose the liquid contact area 14' respectively from outer circumference end parts of the negative electrode sheet 13 and the positive electrode sheet 15 that face different directions. The same applies to below-described FIGS. 7A to 7C, too.

Figure 4A:
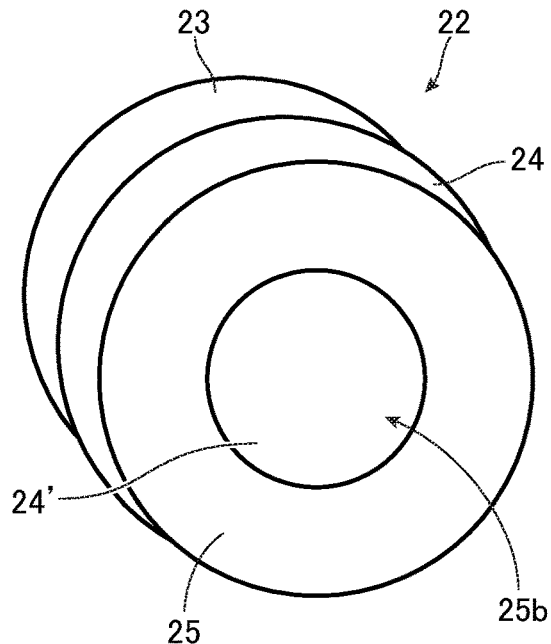
FIG. 4A is an exploded plan view of a liquid detection sensor according to a fourth embodiment.
Figure 4B:
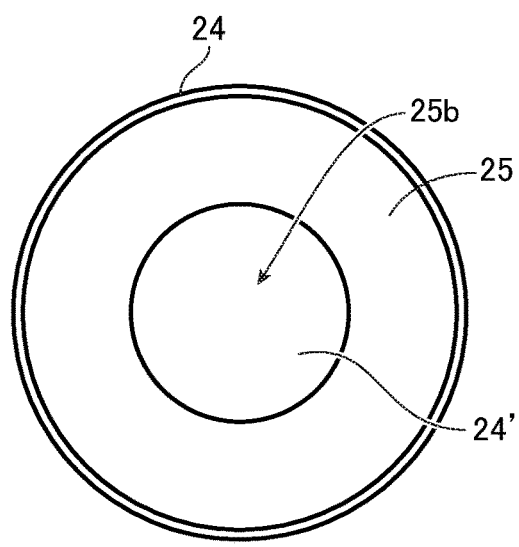
FIG. 4B is a plan view of the liquid detection sensor according to the fourth embodiment.
Figure 4C:
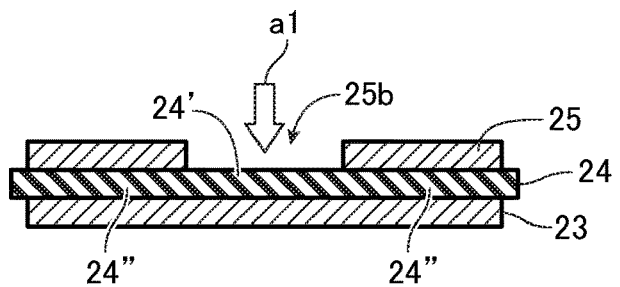
FIG. 4C is a longitudinal cross-sectional view of the liquid detection sensor according to the fourth embodiment.

FIG. 4A is an exploded plan view of a liquid detection sensor according to the fourth embodiment, FIG. 4B is a plan view, and FIG. 4C is a longitudinal cross-sectional view. A metal-air battery 22 illustrated in FIGS. 4A to 4C adopts, for example, a laminated structure formed by laminating a negative electrode sheet 23 of a circular shape, a separator 24 of a circular shape and a positive electrode sheet 25 of a ring shape formed by cutting a center of a circular shape. According to the present embodiment, as illustrated in FIGS. 4B and 4C, one hole 25b that continues to the separator 24 is formed in the positive electrode sheet 25, and a part of the separator 24 that is exposed through the hole 25b is a liquid contact area 24'.

Furthermore, the separator 24 is provided with a detection area 24" on which the negative electrode sheet 23 and the positive electrode sheet 25 overlap with the separator 24 interposed therebetween.

As illustrated in FIG. 4C, a liquid contacts the liquid contact area 24' of the separator 24 from a direction of an arrow a1. Then, the liquid permeates from the liquid contact area 24' to the detection area 24", so that reactions indicated by above (1) to (3) occur, and electric power is discharged.

In addition, the negative electrode sheet 23 may be formed in, for example, a ring shape, and the positive electrode sheet 25 may be formed in a circular shape similar to that of the separator 24. In this case, a part of the separator 24 that is exposed through a hole formed in the center of the negative electrode sheet 23 is the liquid contact area 24'. According to this structure, for example, the negative electrode sheet 23 is disposed facing a side that contacts the liquid. In this case, even when the amount of the liquid is large and the negative electrode sheet 23 side is blocked from contacting air, as long as the positive electrode sheet 25 side can keep contact with the air, it is possible to cause the metal-air battery 22 to appropriately operate. Therefore, in a case where the amount of a liquid that contacts the metal-air battery 22 is large, it is preferable to form the negative electrode sheet 23 side of a small area, and provide the liquid contact area 24' on an inner side of the outer circumference end part of the negative electrode sheet 23. In addition, both of the negative electrode sheet 23 and the positive electrode sheet 25 may be formed in, for example, ring shapes. Even when a liquid contacts either one side of the negative electrode sheet 23 side and the positive electrode sheet 25 side, it is possible to detect the liquid.

Figure 5A:
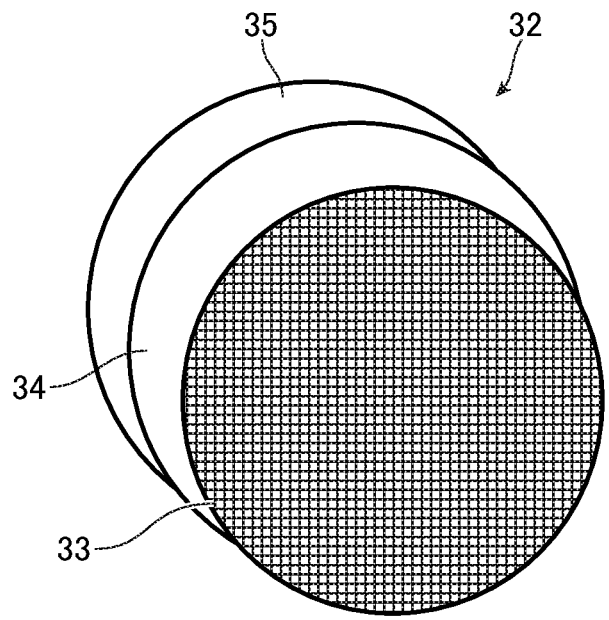
FIG. 5A is an exploded plan view of a liquid detection sensor according to a fifth embodiment.
Figure 5B:
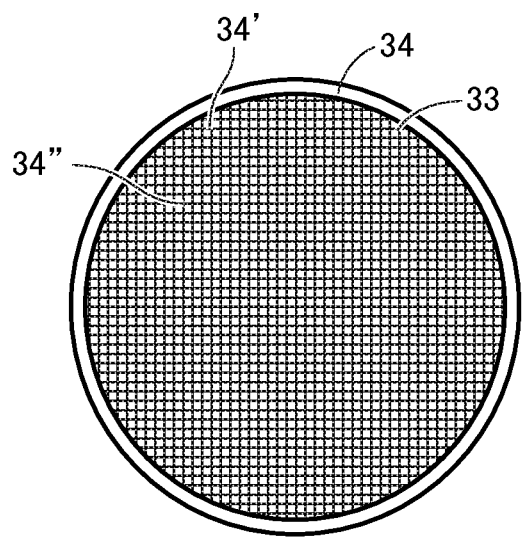
FIG. 5B is a plan view of the liquid detection sensor according to the fifth embodiment.
Figure 5C:
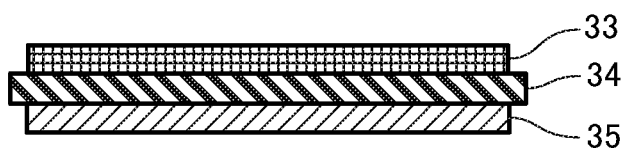
FIG. 5C is a longitudinal cross-sectional view of the liquid detection sensor according to the fifth embodiment.

FIG. 5A is an exploded plan view of a liquid detection sensor according to the fifth embodiment, FIG. 5B is a plan view, and FIG. 5C is a longitudinal cross-sectional view. A metal-air battery 32 illustrated in FIGS. 5A to 5C adopts, for example, a laminated structure formed by laminating a positive electrode sheet 35 of a circular shape, a separator 34 of a circular shape and a negative electrode sheet 33 of a mesh shape. Multiple micropores are formed in the negative electrode sheet 33 of the mesh shape, and a part of the separator 34 that is exposed through each micropore is a liquid contact area 34'.

Furthermore, a part of the separator 34 other than the liquid contact areas 34' is a detection area 34" (a part at which the negative electrode sheet 33 and the positive electrode sheet 35 overlap with the separator 34 interposed therebetween).

In addition, in FIGS. 5B and 5C, a structure that the negative electrode sheet 33 is a side that contacts a liquid, and the positive electrode sheet 35 contacts air is secured.

When a liquid contacts the liquid contact areas 34' of the separator 34 through the negative electrode sheet 33 of the mesh shape, the liquid permeates from the liquid contact areas 34' to the detection areas 34", so that reactions indicated by above (1) to (3) occur, and electric power is discharged.

According to the fifth embodiment, the positive electrode sheet 35 may have a mesh shape. In this regard, for use in a case of a large liquid leakage amount, it is preferable to form the negative electrode sheet 33 in the mesh shape and secure contact of the negative electrode sheet 33 side with the liquid to reliably keep contact of the positive electrode sheet 35 with air. In addition, both of the negative electrode sheet 33 and the positive electrode sheet 35 may have the mesh shapes.

Figure 6A:
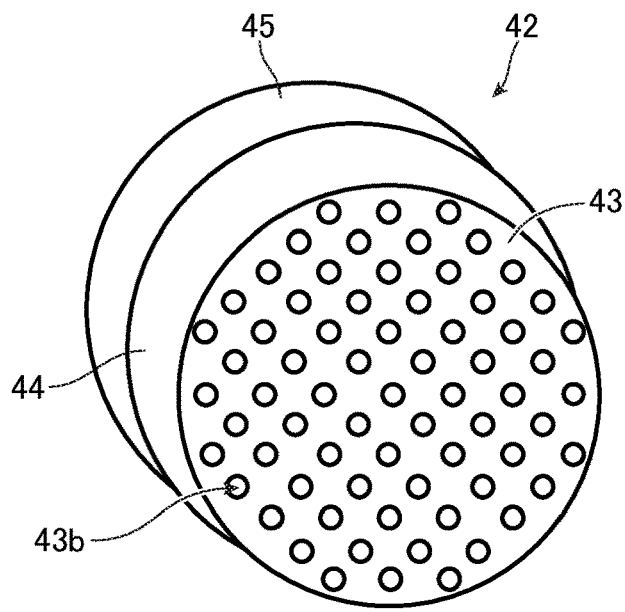
FIG. 6A is an exploded plan view of a liquid detection sensor according to a sixth embodiment.
Figure 6B:
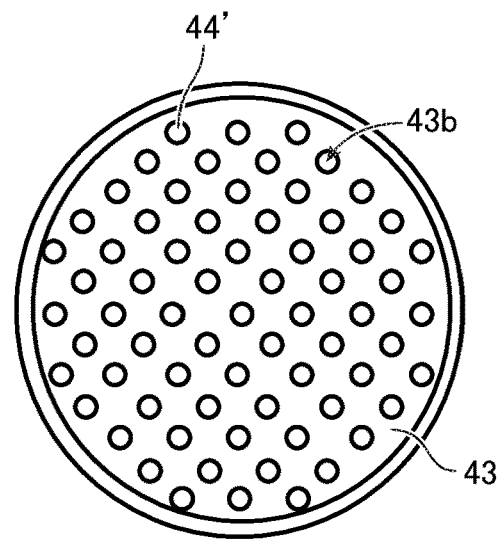
FIG. 6B is a plan view of the liquid detection sensor according to the sixth embodiment.
Figure 6C:
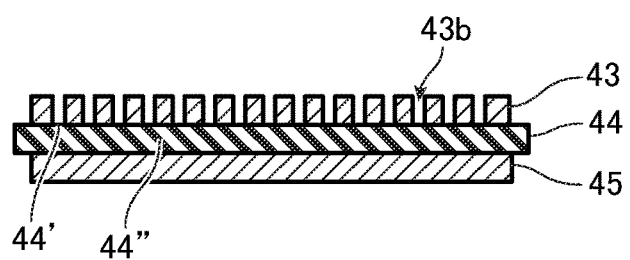
FIG. 6C is a longitudinal cross-sectional view of the liquid detection sensor according to the sixth embodiment.

FIG. 6A is an exploded plan view of a liquid detection sensor according to the six embodiment, FIG. 6B is a plan view, and FIG. 6C is a longitudinal cross-sectional view. A metal-air battery 42 illustrated in FIGS. 6A to 6C adopts, for example, a laminated structure formed by laminating a positive electrode sheet 45 of a circular shape, a separator 44 of a circular shape and a negative electrode sheet 43 in which a plurality of small holes 43b are formed. For example, the plurality of small holes 43b can be formed in the negative electrode sheet 43 by, but not limited to, punching. A part of the separator 44 that is exposed through each small hole 43b is a liquid contact area 44'.

Furthermore, a part of the separator 44 other than the liquid contact areas 44' is a detection area 44" (a part at which the negative electrode sheet 43 and the positive electrode sheet 45 overlap with the separator 44 interposed therebetween).

In FIGS. 6A to 6C, the small holes 43b are evenly and regularly formed in the negative electrode sheet 43. However, it is also possible to form the small holes 43b only in part of an area of the negative electrode sheet 43. For example, it is possible to intensively form the small holes 43b at a site at which a liquid contact amount is large.

When a liquid contacts the liquid contact areas 44' of the separator 44 through the small holes 43b of the negative electrode sheet 43, the liquid permeates from the liquid contact areas 44' to the detection area 44", so that reactions indicated by above (1) to (3) occur, and electric power is discharged.

According to the sixth embodiment, a plurality of small holes may be formed in the positive electrode sheet 45. In this regard, for use in a case of a large liquid leakage amount, it is preferable to form the plurality of small holes 43b in the negative electrode sheet 43 and secure contact of the negative electrode sheet 43 side with the liquid to reliably keep contact of the positive electrode sheet 45 with air. In addition, the plurality of small holes 43b may be formed in both of the negative electrode sheet 43 and the positive electrode sheet 45.

Figure 7A:
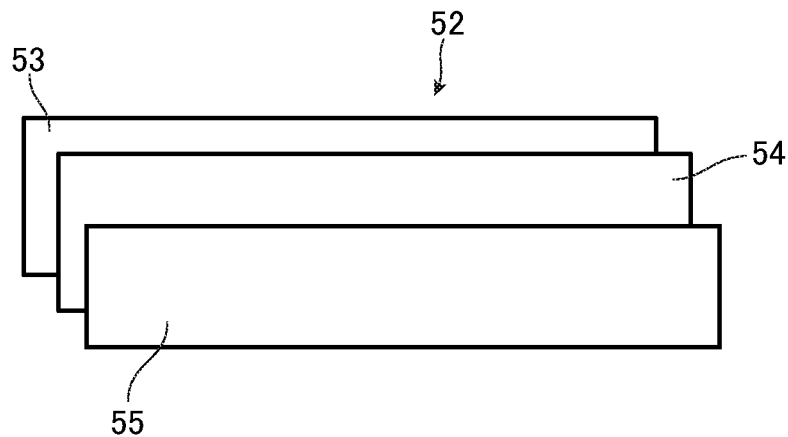
FIG. 7A is an exploded plan view of a liquid detection sensor according to a seventh embodiment.
Figure 7B:
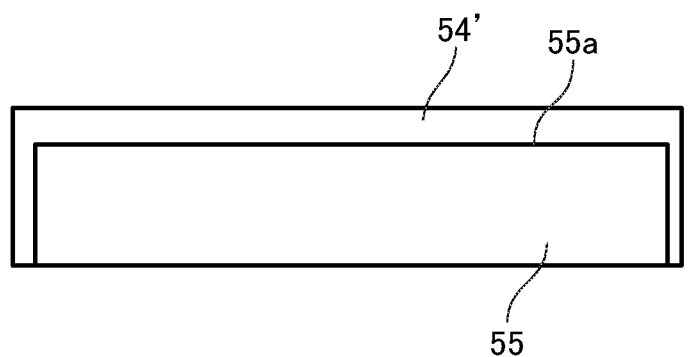
FIG. 7B is a plan view of the liquid detection sensor according to the seventh embodiment.
Figure 7C:
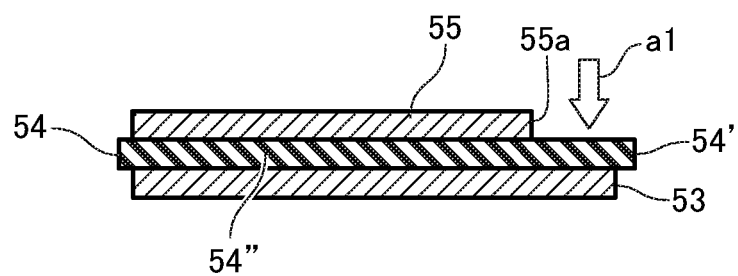
FIG. 7C is a longitudinal cross-sectional view of the liquid detection sensor according to the seventh embodiment.

FIG. 7A is an exploded plan view of a liquid detection sensor according to the seventh embodiment, FIG. 7B is a plan view, and FIG. 7C is a longitudinal cross-sectional view.

According to a metal-air battery 52 illustrated in FIGS. 7A to 7C, although each of a negative electrode sheet 53, a separator 54 and a positive electrode sheet 55 has, for example, a rectangular shape, the positive electrode sheet 55 has a narrower width than those of the negative electrode sheet 53 and the separator 54. Hence, in a laminated structure formed by laminating the negative electrode sheet 53, the separator 54 and the positive electrode sheet 55, a liquid contact area 54' is exposed from the separator 54 outward from an outer circumference end part 55a of one side of the positive electrode sheet 55 as illustrated in FIGS. 7B and 7C.

Furthermore, the separator 54 is provided with a detection area 54" in which the negative electrode sheet 53 and the positive electrode sheet 55 overlap with the separator 54 interposed therebetween.

When a liquid contacts the liquid contact areas 54' of the separator 54 from a direction of an arrow a1 as illustrated in FIG. 7C, the liquid permeates from the liquid contact areas 54' to the detection area 54", so that reactions indicated by above (1) to (3) occur, and electric power is discharged.

In addition, there may be adopted a structure that the width of the negative electrode sheet 53 is reduced, and the liquid contact area 54' of the separator 54 is provided on an outer side of the outer circumference end part of one side of the negative electrode sheet 53.

According to this structure, for example, the negative electrode sheet 53 is disposed facing a side that contacts the liquid. In this case, even when the amount of the liquid is large and the negative electrode sheet 53 side is blocked from contacting air, as long as the positive electrode sheet 55 side can keep contact with the air, it is possible to cause the metal-air battery 52 to appropriately operate. Therefore, in a case where the amount of a liquid that contacts the metal-air battery 52 is large, it is preferable to form the negative electrode sheet 53 side of a small area, and provide the liquid contact area 54' to the outer circumference end part of the negative electrode sheet 53.

As described in, for example, the third embodiment illustrated in FIGS. 3A to 3C and the seventh embodiment illustrated in FIGS. 7A to 7C, the positive electrode sheets (negative electrode sheets) are formed in the cutout shape and the shape of the narrowed width to form the liquid contact areas of the separators that protrude from the outer circumference end parts of the positive electrode sheets (negative electrode sheets). However, these shapes are mere examples, and do not limit shapes. Furthermore, for example, an outer shape of a metal-air battery 12 is a circular shape in the third embodiment illustrated in FIGS. 3A to 3C, and an outer shape of the metal-air battery 52 is the rectangular shape in the seventh embodiment illustrated in FIGS. 7A to 7C. However, these shapes are mere examples, and do not limit shapes. The same applies to the other embodiments, too.

Figure 8A:
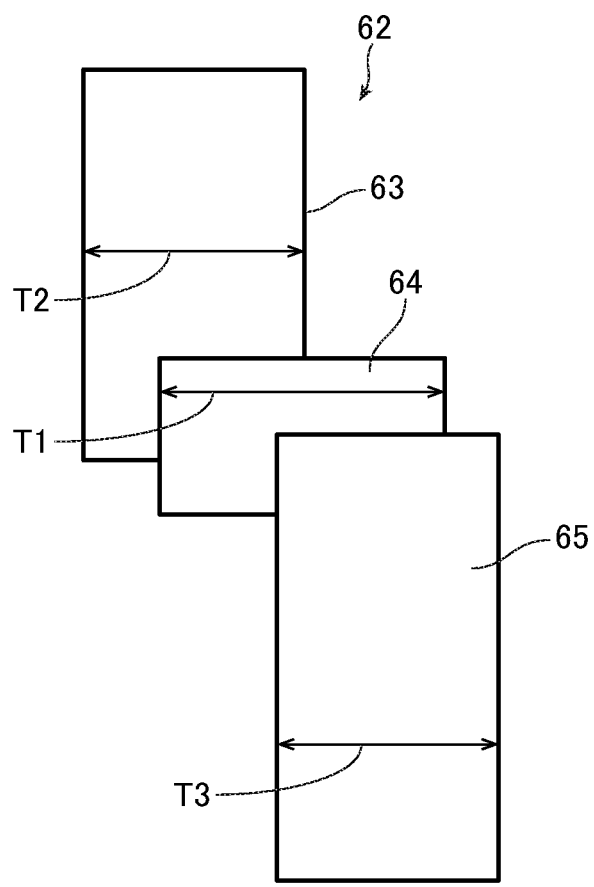
FIG. 8A is an exploded plan view of a liquid detection sensor according to an eighth embodiment.
Figure 8B:
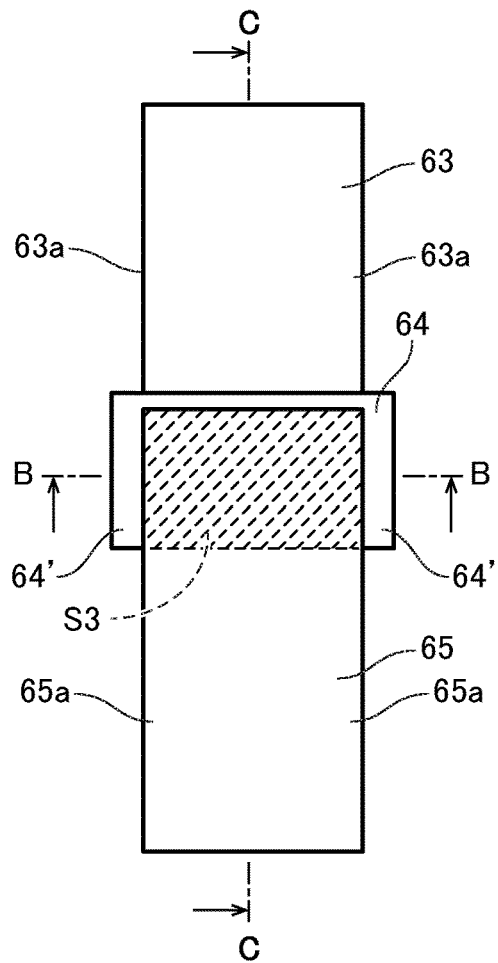
FIG. 8B is a plan view of the liquid detection sensor according to the eighth embodiment.
Figure 8C:
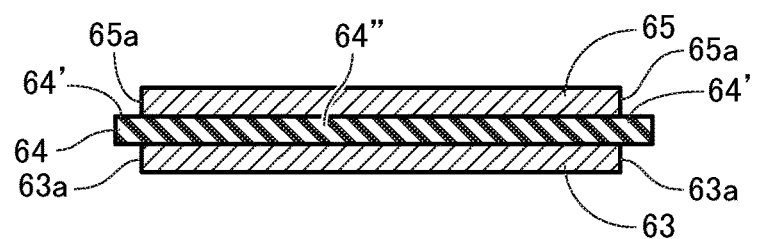
FIG. 8C is a longitudinal cross-sectional view cut along a line B-B in FIG. 8B and seen from an arrow direction.
Figure 8D:
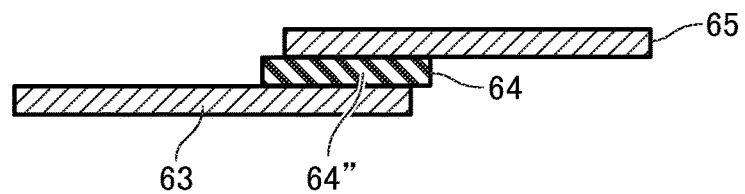
FIG. 8D is a longitudinal cross-sectional view cut along a line C-C in FIG. 8B and seen from an arrow direction.

According to the embodiments illustrated in FIGS. 1 to 7, each separator is formed to have a wider area than those of each positive electrode sheet and each negative electrode sheet. However, for example, as illustrated in FIGS. 8A to 8D, a separator 64 can be also formed to have an area smaller than those of a negative electrode sheet 63 and a positive electrode sheet 65. In this regard, as illustrated in FIG. 8A, a width dimension T1 of the separator 64 is wider than each of width dimensions T2 and T3 of the negative electrode sheet 63 and the positive electrode sheet 65. Therefore, in a case of the metal-air battery 62 that adopts a laminated structure formed by laminating the negative electrode sheet 63, the separator 64 and the positive electrode sheet 65, as illustrated in FIGS. 8B and 8C, the separator 64 is provided with liquid contact areas 64' that are exposed outward from outer circumference end parts 63a and 65a of the negative electrode sheet 63 and the positive electrode sheet 65. Furthermore, the separator 64 is provided with a detection area 64" in which the negative electrode sheet 63 and the positive electrode sheet 65 overlap with the separator 64 interposed therebetween.

When a liquid contacts the liquid contact area 64' of the separator 64, the liquid permeates from the liquid contact area 64' to the detection area 64", so that reactions indicated by above (1) to (3) occur, and electric power is discharged.

Figure 9A:
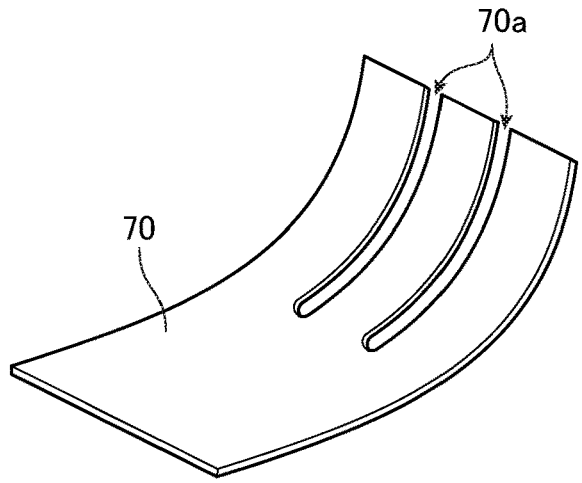
FIG. 9A is a perspective view of a liquid detection sensor according to a ninth embodiment.
Figure 9B:
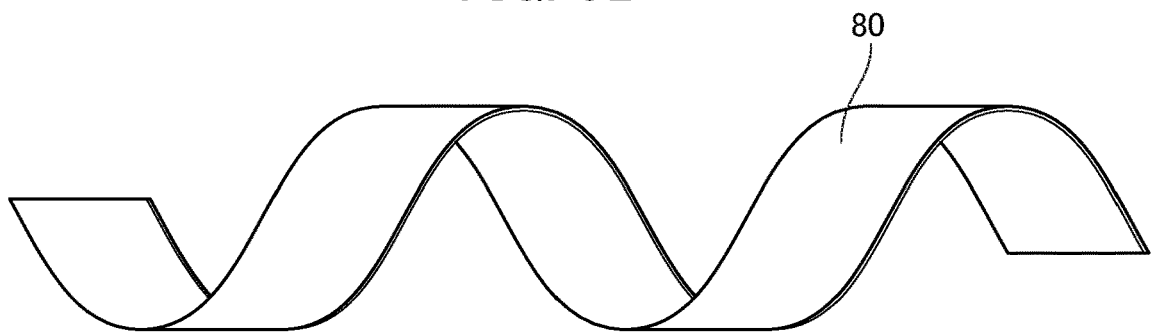
FIG. 9B is a perspective view of a liquid detection sensor according to a tenth embodiment.

The metal air-battery according to each of the above-described embodiments has flexibility. Therefore, not only the metal-air battery can have a planar shape, but also, for example, part of a metal-air battery 70 can be bent in a curved shape as illustrated in FIG. 9A, and a metal-air battery 80 can be deformed in a spiral shape as illustrated in FIG. 9B. Furthermore, by forming cutouts 70a in the metal-air battery 70 as illustrated in FIG. 9A, it is possible to easily divide the metal-air battery 70 into a plurality of parts.

Conventionally, a liquid absorbable member or the like has been provided separately from a battery section to make a liquid permeate to a separator. However, according to the present embodiment, a separator is formed wider than an area in which a positive electrode sheet and a negative electrode sheet overlap with the separator interposed therebetween. In each of the above embodiments, "the area in which the positive electrode sheet and the negative electrode sheet overlap with the separator interposed therebetween" corresponds to an area of a detection area of the separator. Describing this area with reference to, for example, FIG. 1B, "the area in which the positive electrode sheet and the negative electrode sheet overlap with the separator interposed therebetween" is equal to an area S1 of a negative electrode sheet 3 and a positive electrode sheet 5. Furthermore, as illustrated in FIG. 1B, the separator 4 is formed to have a wider area than the area S1. Furthermore, taking FIGS. 3B and 3C as examples, "the area in which the positive electrode sheet and the negative electrode sheet overlap with the separator interposed therebetween" is equal to an area S2 of a positive electrode sheet 15. A negative electrode sheet 13 has a wider area than that of the positive electrode sheet 15, and therefore the entire negative electrode sheet 13 does not overlap the positive electrode sheet 15. On the other hand, the entire positive electrode sheet 15 overlaps the negative electrode sheet 13, and therefore "the area in which the positive electrode sheet and the negative electrode sheet overlap with the separator interposed therebetween" is the area S2 of the positive electrode sheet 15.

Furthermore, taking FIG. 8B as an example, "the area in which the positive electrode sheet and the negative electrode sheet overlap with the separator interposed therebetween" is equal to an area S3 in which a negative electrode sheet 63 and a positive electrode sheet 65 overlap.

Furthermore, in the present embodiment, the separator includes the liquid contact area that is exposed from at least one of the positive electrode sheet and the negative electrode sheet. That is, the separator is formed wider than the area in which the positive electrode sheet and the negative electrode sheet overlap with the separator interposed therebetween, and therefore the separator includes the area that protrudes from at least one of the positive electrode sheet and the negative electrode sheet. This area is the liquid contact area. Consequently, it is possible to absorb a liquid in the liquid contact area, and make the liquid permeate to the detection area in which the positive electrode sheet and the negative electrode sheet overlap with the separator interposed therebetween, so that it is possible to accurately detect even a small amount of the liquid.

Furthermore, according to each embodiment, the separator is provided with the liquid contact area integrally with the detection area, so that it is possible to make a liquid smoothly permeate to the detection area of the separator without increasing the number of parts, and precisely detect liquid leakage. Furthermore, it is possible to realize a liquid detection sensor 1 that is thin and has a high degree of freedom of an installation place.

As illustrated in FIG. 10, the liquid detection sensor 1 according to the present embodiment includes a metal-air battery 2 and a transmission section 6. In the metal-air battery 2, a cell reaction based on liquid leakage changes a voltage value (resistance value). A detection signal based on this voltage change is transmitted by radio from the transmission section 6 to a reception section 7. The reception section 7 can detect occurrence of liquid leakage based on the received detection signal, automatically stop an apparatus or the like, and broadcast the occurrence of liquid leakage to people. It is possible to use a threshold for the detection signal, and judge that liquid leakage has occurred or decide a liquid leakage level when a level of the detection signal exceeds the threshold. In addition, FIG. 10 generically uses the reference numeral of the metal-air battery illustrated in FIGS. 1 and 2 for the metal-air battery. However, the liquid detection sensor 1 in FIG. 10 is naturally applicable to the metal-air batteries according to the other embodiments, too.

The liquid detection sensor 1 according to the present embodiment includes the metal-air battery, and privately generates electric power by water leakage or blood leakage. In this regard, the separator needs to contain salt in advance to privately generate electric power by water leakage. Salt is, but not limited to, for example, sodium chloride. Thus, according to the present embodiment, the liquid detection sensor 1 does not need an external power supply, and can transmit the detection signal obtained by the metal-air battery by radio from the transmission section 6 to the reception section 7. A radio scheme is not limited, and existing schemes such as wireless LAN, Bluetooth (registered trademark) and Wi-Fi can be used for the radio scheme.

As described above, according to the present embodiment, the liquid detection sensor 1 does not need to use a wire, can be realized in a compact form, does not make cords bothering when the liquid detection sensor 1 according to the present embodiment is attached to a human body, and, moreover, can be easily attached to sites where the liquid detection sensor 1 is difficult to install.

Although usage of the liquid detection sensor 1 according to the present embodiment is not limited, the liquid detection sensor 1 can be applied to medical settings or indoor workplaces.

At the medical settings, the liquid detection sensor 1 can detect intravenous drip leakage or blood leakage. For blood leakage, the liquid detection sensor 1 can be used as a blood leakage sensor for dialysis. As in the embodiment illustrated in FIG. 2, in the case of the liquid detection sensor 1 whose separator 4 is bent, the entire lower face of the liquid detection sensor 1 is a liquid contact area 4', so that, by applying the liquid detection sensor 1 near a syringe inserted in a patient's skin, it is possible to quickly detect bleeding from a puncture portion.

The liquid detection sensor according to the present invention can be effectively applied as a blood leakage detection sensor and a water leakage detection sensor. More particularly, the present invention can realize a thin and small liquid detection sensor, and the liquid detection sensor does not need an external power supply. Consequently, the liquid detection sensor provides excellent user friendliness, and can be easily used irrespectively of targets and sites.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A liquid detection sensor comprising:
   a metal-air battery that is formed by laminating a positive electrode sheet, a negative electrode sheet and a separator interposed between inner faces of the positive electrode sheet and the negative electrode sheet; and
   a reception section that receives a detection signal derived from the metal-air battery,
   wherein the separator is formed larger than an area in which the positive electrode sheet and negative electrode sheet overlap with the separator interposed therebetween,
   wherein the separator protrudes from multiple edges of the overlapping positive electrode sheet and the negative electrode sheet, and protrudes from one of the multiple edges of the negative electrode sheet and of the positive electrode sheet by a longer amount than the other edges to form a liquid contact area,
   whereby the separator defines:
      a detection area between the inner faces of the overlapping positive electrode sheet and negative electrode sheet, the detection area generating the detection signal when permeated by a liquid, and
      the liquid contact area, and
   wherein the liquid contact area is connected with the detection area between the overlapping positive and negative electrode sheets, extends from the detection area at the one edge of the negative electrode sheet, and bends around the one edge of the negative electrode sheet to a position that overlaps an outer face of the negative electrode sheet and exposes the liquid contact area remote from the positive electrode sheet,
   whereby when a liquid contacts the exposed liquid contact area positioned at the outer face of the negative electrode sheet, the liquid permeates the liquid contact area up to the detection area sandwiched between the positive electrode sheet and the negative electrode sheet, and generates the detection signal, and
   the reception section is responsive to the detection signal and signals a leakage of liquid when a level of the detection signal exceeds a threshold.

2. The liquid detection sensor according to claim 1, wherein the liquid contact area is formed by being bent such that a part extending from edges of both of the positive electrode sheet and the negative electrode sheet overlaps the outer face of the negative electrode sheet.

3. The liquid detection sensor according to claim 1, wherein
   a thickness of the positive electrode sheet is 0.4 mm to 2.0 mm, and a thickness of the negative electrode sheet is 0.05 mm to 2.0 mm.

4. The liquid detection sensor according to claim 1, wherein
   an outer sheet that covers a surface of a laminated part at which the positive electrode sheet, the negative electrode sheet and the separator are laminated is provided, and
   the outer sheet is disposed such that air can contact the positive electrode sheet.

5. The liquid detection sensor according to claim 1, wherein
   the separator is separated into a plurality of separators, and the liquid contact area is formed with each separator.

6. The liquid detection sensor according to claim 1, wherein the negative electrode sheet is a magnesium sheet or a magnesium alloy sheet.

7. The liquid detection sensor according to claim 1, comprising a transmission section that can communicate the detection signal of the metal-air battery by radio to the reception section.

8. The liquid detection sensor according to claim 1, wherein the liquid detection sensor is a blood leakage detection sensor.

9. The liquid detection sensor according to claim 1, wherein the liquid detection sensor is a water leakage detection sensor.

* * * * *